United States Patent [19]

Gilmour et al.

[11] 4,346,074

[45] Aug. 24, 1982

[54] PASTEURELLOSIS VACCINES

[75] Inventors: Neil J. L. Gilmour, Falkirk; William B. Martin, Longniddry; James M. Sharp, Haddington, all of Scotland; Dennis A. Thompson, Hayes, England; Peter W. Wells, Haddington, Scotland

[73] Assignee: National Research Development Corp., London, England

[21] Appl. No.: 194,122

[22] PCT Filed: Aug. 16, 1979

[86] PCT No.: PCT/GB79/00141

§ 371 Date: Apr. 23, 1980

§ 102(e) Date: Apr. 23, 1980

[87] PCT Pub. No.: WO80/00412

PCT Pub. Date: Mar. 20, 1980

[30] Foreign Application Priority Data

Aug. 24, 1978 [GB] United Kingdom ............... 34525/78

[51] Int. Cl.³ .................... A61K 39/00; A61K 39/102
[52] U.S. Cl. .......................................... 424/92; 424/88
[58] Field of Search ..................... 424/92, 87, 88, 177; 435/253

[56] References Cited

U.S. PATENT DOCUMENTS 3,526,696 9/1970 Gale et al. .............................. 424/92

OTHER PUBLICATIONS

Derwent Abstract No. 00385C/01, Great Britain Patent 2023420, 1978.

Mukkur et al., Am. J. Vet. Res, vol. 39, pp. 1269–1273, 1978.

Mukkur, Injection and Immunity, vol. 18, pp. 583–585 (1977).

Ganfield, et al., Injection and Immunity, vol. 14, pp. 990–999 (1976).

Thompson et al., "Serotypes of *Pasteurella Haemolytica* in Ovine Pasteurellosis", Research in Veterinary Science 1977, 22, 130–1.

Mukkur, T. K. S., "Demonstration of Cross-Protection between *Pasteurella Multocida* type A and *Pasteurella Haemolytica* Serotype 1", Infection and immunity, Dec. 1977, vol. 18, No. 3, pp. 583–585.

Penn et al., "Capsular and Somatic Antigens of *Pasteurella Multocida*, types B and E", Res. Vet. Sci. 1974, 16, 251–259.

*Primary Examiner*—Blondel Hazel
*Attorney, Agent, or Firm*—Oblon, Fisher, Spivak, McClelland & Maier

[57] ABSTRACT

A pasteurella vaccine e.g. for use with cattle or particularly sheep, comprises antigenic material derived from the A1 and A2 serotypes of *Pasteurella haemolytica*, the A1 serotype antigenic material comprising capsular extract, e.g. especially salicylate extract, and the A2 serotype antigenic material comprising heat-killed whole organisms, and a process for the production of a pasteurellosis vaccine comprises preparing said antigenic material from *P. haemolytica* organisms and formulating the antigenic material into a vaccine, e.g. especially an aluminium hydroxide gel/oil adjuvant vaccine. Also a method for use in agricultural animal husbandry for the prevention and control of pasteurellosis in sheep, cattle and other animals comprises vaccinating the animals with a vaccine according to the invention.

22 Claims, No Drawings

PASTEURELLOSIS VACCINES

This invention relates to pasteurellosis vaccines their production and use for the prevention and control of pasteurellosis in sheep, cattle and other animals.

Pasteurellosis is a common respiratory disease of sheep and cattle which may often lead to fatality, particularly in the case of young animals, and thus the prevention and control of this disease is of great importance to farmers engaged in the rearing of sheep and cattle. In sheep the disease appears as either a pneumonia or a septicaemic condition dependent upon the age of the infected animal and the strain of the infecting organism, whereas in cattle the disease is encountered primarily as a penumonia in regions with temperate climates. *Pasteurella haemolytica* has been identified as the main causative agent of the disease in sheep, and two of the serotypes of this organism together with strains of an associated organisms, *Pasteurella multocida*, appear to be responsible for the pneumonic disease of cattle. Two biotypes of *P. haemolytica* have been identified, the A biotype generally associated with septicaemias in young lambs and pneumonias in older sheep, and the T biotype generally associated with septicaemias in adult sheep, and within these two biotypes twelve different serotypes have been identified. Only the A biotypes but not the T biotypes of *P. haemolytica* appear to be involved in cattle pneumonias.

At present vaccines are commercially available for use in the prevention and control of pasteurellosis in sheep and cattle, the sheep vaccines comprising formalin killed organisms of a range of serotypes of *P. haemolytica*. These vaccines, however, do not appear to provide satisfactory protection against pasteurellosis. It has now been found that effective pasteurellosis vaccines for sheep and possibly cattle can be prepared if careful attention is paid to the source and method of formulation of the *P. haemolytica* antigenic material which is incorporated into the vaccines.

The various serotypes of *P. haemolytica* as hereinafter referred to e.g. the A1 and A2 serotypes, may be determined by methods previously described and understood in the art; for instance, as determined by the serotyping methods described by Biberstein et al (Biberstein, E. L., Gills, M., & Knight H. (1960) Cornell Veterinarian 50, page 283).

According to the present invention a pasteurella vaccine comprises antigenic material derived from the A1 and A2 serotypes of *Pasteurella haemolytica*, in which the A1 serotype antigenic material comprises capsular extract and the A2 serotype antigenic material comprises heat-killed whole organisms.

The invention also includes processes for the production of pasteurellosis vaccines in which antigenic material from the A1 and A2 serotypes of *P. haemolytica*, comprising capsular extract of the A1 serotype and heat-killed whole organisms of the A2 serotype, is prepared from *P. haemolytica* organisms and formulated into a vaccine. Furthermore the invention also includes methods for use in agricultural animal husbandry for the prevention and control of pasteurellosis in sheep, cattle and other animals which comprises vaccinating the animals with a vaccine according to the invention.

Vaccines according to the invention may be used in agricultural applications for the prevention and control of pasteurellosis in general to combat both animal losses and inefficient meat production due to the disease. In particular vaccines according to the invention are suitable for vaccination of sheep and cattle. Generally the vaccines may contain further antigenic material in addition to antigenic material derived from the *P. haemolytica* A1 and A2 serotypes, and it will be appreciated that the nature of such further antigenic material may depend upon the species of animal and form of disease for which the vaccine is intended. Thus, in addition to antigenic material derived from the A1 and A2 serotypes of *P. haemolytica*, vaccines for sheep may comprise antigenic material derived from other serotypes of *P. haemolytica*, and vaccines for cattle typically comprise antigenic material derived from strains of *P. multocida*. Furthermore, for example, sheep vaccines which are intended specifically to combat only the pneumonic form of the disease in adult sheep may comprise antigenic material derived from the A serotypes only of *P. haemolytica*. Alternatively sheep vaccines intended for combatting both the septicaemic and pneumonic forms of the disease typically comprise antigenic material derived from a combination of A and T serotypes.

Preferably sheep vaccines according to the invention comprise antigenic material derived from the A6 serotype of *P. haemolytica*, and in one embodiment there is provided a trivalent vaccine comprising A1, A2 and A6 serotype antigenic material for use in combating pneumonias in adult sheep. Alternatively, or preferably in addition, sheep vaccines may comprise antigenic material derived from the A9 serotype, and especially also the A7 serotype. Furthermore sheep vaccines for combating both pneumonic and septicaemic pasteurellosis, in addition to additional A serotype antigenic material e.g. A6, preferably A6+A9, or especially A6+A9+A7 serotype antigenic material, comprise T serotype antigenic material, preferably a combination of T3, T4 and T10 serotype antigenic material.

Cattle vaccines typically comprise antigenic material derived from suitable strains of *P. multocida* such as, for instance, types A and D (Carter, G. R. (1955) Am. J. Vet. Res. 18, page 481), preferably a combination of the A and D types of *P. multocida*.

In addition to the additional antigenic material derived from species of Pasteurellae, the vaccines of the invention may include antigenic material derived from other organisms including other bacteria and also viruses. Thus, for example, the vaccine may also include antigenic material derived from viruses associated with Pasteurella organisms in the aetiology of Pasteurellosis, such as, for instance, antigenic material derived from parainfluenza virus e.g. parainfluenza virus type 3 (PI3).

The additional antigenic material, besides that derived from the A1 and A2 serotypes, included within the vaccines of the invention, may take any suitable form, though, preferably is of high immunogenic and antigenic character. Thus the additional Pasteurella antigenic material may comprise killed whole organisms of *P. haemolytica* and/or *P. multocida*, preferably heat-killed whole organisms. Especially, however, the additional antigenic material comprises an extract of *P. haemolytica* and/or *P. multocida*, e.g. a capsular extract. In this latter respect it has been found, according to the present invention, that capsular extracts of *P. haemolytica* generally exhibit advantageous antigenic properties, particularly desirable for vaccine formulation, as compared with killed whole organisms, such as formalin killed whole organisms. It is thus particularly surprising that heat-killed whole organisms of the A2 serotype of

*P. haemolytica* provide a material having significantly better antigenic properties than a capsular extract.

Furthermore, however, in particular embodiments of the present invention it may be desirable to include A2 capsular extract antigenic material in the vaccine together with the A2 antigenic material comprising heat killed whole organisms. It is believed that such combination of capsular extract and heat killed whole organisms of *P. haemolytica* A2 serotype may give rise to enhanced antigenic and immunogenic properties as compared with vaccines containing A2 heat killed whole organism alone, in particular for use in vaccines containing antigenic material derived from several serotypes e.g. at least three, of *P. haemolytica* and/or other organisms.

The capsular extract antigenic material of the vaccines of the invention typically comprises polysaccharide capsule material and may be prepared as an extract from whole cells by any suitable extraction procedure such as those which are known to workers skilled in the vaccine production and immunology art e.g., extraction with saline solution. Preferably, however, the capsular extract antigenic material comprises protein and especially also lipopolysaccharide antigenic material in addition to capsule polysaccharide antigenic material. It is believed that inclusion of these additional protein and lipopolysaccharide cell components in the capsular extract gives rise to enhanced antigenic and immunogenic properties as compared with capsular extracts containing predominantly only polysaccharide capsule material. Capsular extracts containing these additional components may be prepared from cells by use of suitable extraction treatments, such as use of thiocyanate solutions, Cetavlon or Cetrimide. A particularly preferred extraction treatment for preparation of protein and lipopolysaccharide containing capsular extracts for use in the vaccines of the invention is treatment with salicylate e.g. aqueous sodium salicylate.

In the preparation of vaccines of the invention the appropriate organisms are grown or otherwise obtained, the corresponding antigenic material is obtained from the organisms and is formulated into the vaccine. Capsular extract antigenic material may be obtained from the organisms by any suitable technique. For example, whole organisms are treated with salicylate e.g. sodium salicylate at concentrations in the range from about 0.1 M up to about 10 M, especially about 1 M, preferably with agitation, for a period of from about 1 up to about 5 hours, especially about 3 hours, cell debris is removed e.g. by centrifugation, and the soluble antigenic product is purified and concentrated. Antigenic material comprising killed whole organism may be prepared from live organisms by any suitable method including use of formalin treatment. Preferably, however, or in the specific case of the A2 serotype antigenic material, whole organism antigenic material is prepared by heat-treatment of live organisms. For example, the live organisms are heat treated at a temperature of at least 50° C. for a period of at least 10 minutes, preferably at least 16 minutes e.g. at about 60° C. for about 16 minutes.

The antigenic material, as prepared above or otherwise, is incorporated into a vaccine formulation which usually also comprises other components including adjuvants and other materials, such as preservatives. Any suitable adjuvant may be used including complete Freund's adjuvant (CFA) or incomplete Freund's adjuvant (IFA). In a preferred embodiment, however, an aluminium hydroxide gel-oil adjuvant has been found to be particularly suitable for use with the vaccines of the invention, advantageously avoiding some of the undesirable side effects e.g. excessive local inflammation, attendant upon inoculation with vaccines comprising Freund's adjuvants. For example, an especially preferred adjuvant is an Alhydrogel-oil adjuvant, the antigenic material being adsorbed on to Alhydrogel and the resultant suspension emulsified with a suitable oil, such as Bayol F preferably containing 10% Aracel.

The concentration of antigenic material in the vaccine may be varied as desired, for instance, in accordance with the dose rate of the vaccine, and in this respect the normal dose used is generally about 1-2 ml. Generally each dose of vaccine comprises about 0.1 to about 20 mg of antigenic material, especially from about 0.5 mg up to about 10 mg e.g. about 5 mg, of antigenic material of each serotype included within the vaccine.

For prevention and control of pasteurellosis, e.g. for use in agricultural animal husbandry, the vaccines of the invention are administered to the animals, e.g. sheep or cattle, usually in the form of a subcutaneous injection. The animals may be vaccinated soon after birth to provide the animals with protection against pasteurellosis at an early stage in their lives, though it may be desirable to allow a minimum period of time to elapse after birth and before vaccination to allow the immunological system of the animal to develop more fully the ability to respond to the vaccine. For example, in the case of lambs it may be desirable to allow a minimum period of four weeks to elapse between birth and vaccination. Also, vaccination may be carried out at particular periods of the year to provide protection against customary seasonal outbreaks of pasteurellosis. For example sheep flocks may be vaccinated in late spring or thereabouts with vaccines according to the invention comprising *P. haemolytica* A serotype antigenic material to provide protection against the outbreaks of pneumonic pasteurellosis which customarily occur in sheep flocks during the summer.

The present invention for the first time provides an effective vaccine which gives effective protection against pneumonic pasteurellosis in sheep. Advantageously vaccines according to the invention may also be used to provide protection against pasteurellosis in general including septacaemic pasteurellosis in sheep and pneumonic pasteurellosis of cattle.

The invention is further described by way of illustration only in the following examples, which relate to the preparation of pasteurellosis vaccines and to the testing of these vaccines in sheep.

EXAMPLE 1

3 monovalent vaccines are prepared from the A2 serotype of *Pasteurella haemolytica* and are tested in sheep against challenge by an aerosol of the homologous serotype. The three vaccines comprise: 1. heat-killed whole organism (HKO) in an aluminium hydroxide gel (Alhydrogel)/oil adjuvant (AO), 2. capsule extract in complete Freund's adjuvant (CFA) and 3. the same extract in aluminium hydroxide gel (Alhydrogel)-oil adjuvant (AO). The preparation of the three vaccines is as follows:

Vaccine Preparation

HKO in AO

Organisms of *P. haemolytica* serotype A2, strain FA2 are grown, checked for purity and inoculated into Oxoid No. 2. broth which is cultured at 37° C. for 18 hours with agitation. The resultant growth is inoculated into 1.5 liters of Oxoid No. 2 broth which is then incubated for 6 hours under the same conditions. Growth is found to be in the region of $10^9$ organisms per ml, determined by viable counts and by means of an EEL nephelometer. The bacteria are harvested by centrifugation at 4° C. for 20 minutes at 12,000 g. The bacteria are then killed by heat treatment at 60° C. for 16 minutes.

The optimal concentration of heat killed organism for adsorption on to the aluminium hydroxide gel (Alhydrogel, Miles Laboratories, Slough, England) is determined by titration according to the manufacturer's instructions (Miles Laboratories, Slough, England). The antigens are then adsorbed on to the aluminium hydroxide gel and the resultant suspension is emulsified in an equal volume of Bayol F (Esso Petroleum, N.J., USA) containing 10% Aracel A (Sigma Chemical Co., St. Louis, Mo., U.S.A.).

Capsule extract in AO

Serotype A2, strain FA2, organisms are grown and harvested as in the preparation of the HKO in AO vaccine described above. After harvesting, however, the bacteria deposit is suspended in 1.0 M sodium salicylate in distilled water to 1/10 of the original volume. The suspension is then shaken at 37° C. for 3 hours and centrifuged at 2800 g at 4° C. for 40 minutes. The supernatant, in dialysis tubing, is then dialysed against three changes of phosphate buffered saline (pH 7.2) at 4° C. over a period of 48 hours and then concentrated to one third volume by pervaporation at 37° C.

The antigenic activity of the concentrate may be determined by titration in an indirect haemagglutination test against a standard rabbit antiserum to the homologous serotype of *P. haemolytica*. The capsule extract may be freeze dried and stored at −20° C.

As for the HKO vaccine the optimal concentration of capsular antigen is determined by titration, the capsular extract adsorbed on to Alhydrogel and the resultant suspension emulsified with an equal volume of Bayol containing Aracel to give an A2 capsule extract in AO vaccine.

Capsule extract in CFA

Capsule extract of type A2, strain FA2, organisms of *P. haemolytica* is prepared as described above. The A2 capsule extract, at the same concentration as in the capsule extract in AO vaccine, is then incorporated by homogenisation in distilled water into CFA (one part of capsule extract to one part of adjuvant).

Vaccination and Challenge

Groups of seven 2-3 week old, specific pathogen free (SPF), hysterectomy derived, colostrum deprived lambs were vaccinated by subcutaneous injection with 2 ml. aliquots of HKO in AO, capsule extract in AO and capsule extract in CFA vaccine respectively. Eight lambs were left untreated to act as controls. The lambs were bled before vaccination, at approximately 3 week intervals and at necropsy. Eight weeks after vaccination the lambs were infected intranasally and intratracheally with $\log_{10}$ 7.2 TCID$_{50}$ of P13 parainfluenza virus and one week later exposed for 15 minutes to an aerosol containing $3.1 \times 10^5$ *P. haemolytica* type A2, strain FA2, organism per liter. It is estimated that each lamb received a dose of approximately $1.0 \times 10^7$ organisms.

The lambs were observed for 5 days after exposure to the *P. haemolytica* aerosol and clinical scores of the degree of illness suffered were recorded. 6 of the 29 lambs, four in the capsule extract in AO group and two unvaccinated, died or were killed because of severe illness within 5 days of challenge. The remaining lambs were killed in random order between 7 and 10 days after challenge, and the lungs of all lambs were examined for lesions and the scores recorded.

The basis of the clinical scores and lesions scores are as follows: Dullness, pyrexia (>42.8° C.) or abnormal respiration were assigned one point each, and death four points, giving a score for each lamb varying between 0 and 4 on each day. The surface areas of the lesions on the dorsal and ventral aspects of the lung diagrams were measured with a planimeter and expressed as a percentage: 0=no lesions, 5=up to 10%, 10=11 to 25%, 20=>25% of lung surface affected. At the end of the experiment the daily clinical scores for each animal were added together. Statistical differences between the clinical scores, lung lesion scores and total score (clinical+lesion score) of the groups were determined by means of the Mann-Whitney test (Snedecar & Cochrane (1967) Statistical Methods 6th Edn. (page 130)).

The results obtained are given below in Table 1 together with the result of statistical analysis by the Mann-Whitney ranking test.

As can be seen, there was no statistically discernible difference between the clinical scores of any of the vaccinated groups and the unvaccinated controls. However there were significantly lower pneumonic lesion scores in the groups vaccinated with HKO in AO and capsule extract in CFA. The total scores in the HKO in AO vaccinates were significantly different from those of capsule extract vaccinated lambs.

Sera from the lambs was tested for antibodies to *P. haemolytica* serotype A2 by the indirect haemoglutination test (IHA) at 3, 6 and 9 weeks after vaccination and at necropsy. No lambs had detectable antibodies. However, using the Immuno Fluorescent antibody test (FAT), 21 of the 22 vaccinated lambs were found to have detectable antibody 6 weeks after vaccination, and all vaccinates tested at necropsy had titres of between 1/256 to 1/2048.

The results obtained overall indicate the superior immunogenic properties of heat killed whole organisms of A2 serotype as compared with capsule extract, and also indicate the existence of a desirable combination effect of these heat killed organisms with the specific Alhydrogel-oil adjuvant.

TABLE 1

Clinical, Lung Lesion and Total Scores in Lambs Inoculated with *P. haemolytica* Vaccines and challenged with Homologous Strain

| Vaccine | No. of in lambs group | No. died or killed in extremis | Mean Clinical Score (range) | Mean Lesion Score (range) | Mean Total Score (range) |
|---|---|---|---|---|---|
| HKO in AO | 7 | — | 5.85 (0 to 12) | 5.0** (0 to 10) | 10.85** (0 to 22) |
| Capsule | | | | | |

TABLE 1-continued

Clinical, Lung Lesion and Total Scores in Lambs Inoculated with
P. haemolytica Vaccines and challenged with Homologous Strain

| Vaccine | No. of in lambs group | No. died or killed in extremis | Mean Clinical Score (range) | Mean Lesion Score (range) | Mean Total Score (range) |
|---|---|---|---|---|---|
| Extract in CFA | 7 | — | 5.42 (4–7) | 12.1* (5–20) | 17.5 (9–27) |
| Capsule Extract in AO | 8 | 4 | 12.5 (2–20) | 15.6 (5–20) | 28.1 (18–39) |
| Unvaccinated | 7 | 2 | 10.7 (4–18) | 18.5 (10–20) | 29.2 (16–38) |

*Significant difference ($P \leq 0.05$) compared with unvaccinated control group
**Significant difference ($P \leq 0.01$) compared with unvaccinated control group

EXAMPLE 2

A combined heat-killed whole organism (HKO) and capsule extract (CE) monovalent vaccine in an aluminium hydroxide gel/oil adjuvant (AO) is prepared from the A2 serotype of P. haemolytica and is tested in sheep. HKO and CE antigenic material is prepared and formulated into an AO adjuvant vaccine substantially as described in Example 1 to give a vaccine containing 2.2 mg of HKO and 5.6 mg of CE antigenic material per 2 ml dose. A group of ten lambs are vaccinated with 2 ml doses of the vaccine, and this group together with a control group of ten lambs are subsequently challenged with an aerosol of A2 organisms and are monitored for clinical signs of disease and subsequently by post mortem lung examination substantially as previously described. The results obtained are given below in Table 2 indicating effective protection afforded by the combination A2 vaccine.

TABLE 2

Clinical, Lung Lesion and Total Scores in lambs inoculated with
P. haemolytica combination HKO and CE vaccine, and in
unvaccinated lambs after challenge with the homologous strain.

| Group | No. | Clinical | Lesion | Total | Lung Counts/g Lesion | Normal |
|---|---|---|---|---|---|---|
| Vaccinates | 1 | 0 | 5 | 5 | 0 | 0 |
|  | 2 | 3 | 5 | 8 | 0 | 0 |
|  | 3 | 0 | 5 | 5 | 0 | 0 |
|  | 4 | 3 | 5 | 8 | 0 | 0 |
|  | 5 | 6 | 5 | 11 | 0 | 0 |
|  | 6 | 11 | 20 | 31 | $1.5 \times 10^7$ | $1.2 \times 10^6$ |
|  | 7 | 6 | 0 | 6 | — | $5 \times 10^2$ |
|  | 8 | 3 | 5 | 8 | 0 | 0 |
|  | 9 | 0 | 0 | 0 | — | 0 |
|  | 10 | 1 | 0 | 1 | — | 0 |
|  | Mean | 3.3 | 5* | 8.3 |  |  |
| Controls | 1 | 7 | 10 | 17 | $1.6 \times 10^5$ | $2.1 \times 10^3$ |
|  | 2 | 16D | 10 | 26 | $2.6 \times 10^8$ | $4.3 \times 10^7$ |
|  | 3 | 7 | 20 | 27 | $4.8 \times 10^5$ | $1.5 \times 10^5$ |
|  | 4 | 0 | 0 | 0 | — | 0 |
|  | 5 | 16D | 20 | 36 | $5.8 \times 10^8$ | $5.3 \times 10^8$ |
|  | 6 | 17D | 20 | 37 | $1.8 \times 10^8$ | $1 \times 10^8$ |
|  | 7 | 2 | 5 | 7 | 0 | 0 |
|  | 8 | 1 | 5 | 7 | 0 | 0 |
|  | 9 | 1 | 5 | 6 | $1 \times 10^3$ | 0 |
|  | 10 | 17D | 20 | 27 | $9.3 \times 10^7$ | $1.8 \times 10^8$ |
|  | Mean | 8.4 | 11.5 | 19 |  |  |

Ratio $\frac{\text{Mean total Score of Vaccinates}}{\text{Controls}} = 0.43$

D = died
— = not done
*Mann-Whitney $P = 0.05$

EXAMPLE 3

Similarly as for previous Examples a capsule extract (CE) monovalent vaccine in an aluminium hydroxide gel/oil (AO) adjuvant is prepared from the A9 serotype of P. haemolytica and tested in sheep. The A9 vaccine is prepared and tested against homologous challenge substantially as described in previous Examples, the vaccine containing 5.6 mg of CE antigenic material per 2 ml dose. The results obtained are given below in Table 3 indicating a high level of protection against homologous challenge as a result of the use of the A9 monovalent vaccine.

TABLE 3

Mean Scores in lambs inoculated with A9 monovalent vaccine after homologous challenge compared with Mean Scores in unvaccinated lambs.

| Group | Mean Clinical Score | Mean Lesion Score | Mean Total Score |
|---|---|---|---|
| Vaccinates | .3* | 1.0 | 1.3* |
| Controls | 2.2 | 4.4 | 6.7 |

*Significant at the 5% level; the mean lesion score of vaccinates was almost significant at the 5% level.

Ratio $= \frac{\text{Mean Total Score of Vaccinates}}{\text{Controls}} = 0.19$

EXAMPLE 4

Combined P. haemolytica A1 and A2 serotype vaccine

Organisms of P. haemolytica serotype A2, strain FA2 and serotype A1, strain FA1, were grown and harvested as described previously for serotype A2 in Example 1. Capsule extract was prepared from the A1 organisms and A2 organisms were heat-killed, also as described previously. Freeze dried capsule extract of serotype A1 was reconstituted and incorporated by homogenisation in distilled water into CFA or IFA (Difco Laboratories, West Molesey, Surrey, England) (1 part of capsule extract to 1 part of adjuvant). Killed whole organisms of serotype A2 were freeze dried and homogenised in CFA Difco or IFA at the rate of 10 mg/ml of vaccine.

Twenty-one SPF lambs between 9 and 25 days old were randomly allocated into groups of 10 and 11 lambs respectively. The group of 10 were each vaccinated subcutaneously with 1 ml of CFA vaccine containing 19 mg/ml of P. haemolytica type A1, capsule extract and 10 mg/ml of type A2 HKO. One month later the same lambs were re-vaccinated with the same antigens in IFA. Four weeks after the second vaccinations both groups of lambs were infected with P13 virus ($10^{7.3}$ TCID$_{50}$) and one week later with an aerosol of P. haemolytica type A1 and type A2 in equal proportions. As in Example 1, the lambs were exposed in randomly allocated groups of four for 15 minutes. The atmosphere contained $2.7 \times 10^5$ organisms/liter, with both serotypes present in equal proportions. The lambs were examined for signs of clinical illness for a period of 5 days after infection with *P. haemolytica*. Lambs which survived were killed between 7 and 10 days after exposure to the aerosol and the lungs of all lambs were examined for lesions. Clinical and lung lesion scores were determined as in Example 1 and the results obtained are given below in Table 4.

range in vaccinates and controls was similar. Lambs in four groups were vaccinated subcutaneously behind the ear with 2 ml., to each individual, of A0 vaccine containing 0.37 and 0.42 mg/ml of capsule extract of strains FA1 and FA6 respectively and 1.51 mg/ml of HKO of strain FA2. Eight weeks after vaccination all the lambs were infected intranasally and intratracheally with $10^{7.7}TCID_{50}$ of P13 virus. One week later the groups of

TABLE 4

Clinical, Lesion and Total Scores in SPF lambs inoculated with *P. haemolytica* Vaccine and in unvaccinated lambs after challenge

| Group | Challenge P. haemolytica type | No. of lambs died or killed in extremis | Mean Clinical Score (range) | Mean Lesion Score (range) | Mean Total Score (range) |
|---|---|---|---|---|---|
| A1 capsule Extract and A2, HKO (10 lambs) | A1, A2 | — | 5.8** (—to 10) | 6.5** (—to 20) | 12.3** (2 to 29) |
| Unvaccinated (11 lambs) | | 6 | 10.4 (3–14) | 20 | 27.8 (23–34) |

**Significant difference ($P \leq 0.01$) compared with unvaccinated control group Six unvaccinated lambs died or had to be killed within four days of challenge. No vaccinated sheep died. All but one of the vaccinates, however, exhibited some clinical abnormality although their clinical scores were significantly different ($P<0.01$) from those of the unvaccinated lambs. All unvaccinated lambs had pneumonic lesions which involved more than one quarter of the lung surface, whereas two vaccinated lambs had no lesions, five had lesions affecting no more than 10% of the lung surface and three had more extensive lesions. Both the lung lesion scores and total scores were significantly different ($P<0.01$) in the vaccinated and unvaccinated lambs.

Vaccination with this combined A1 and A2 serotype vaccine significantly reduces the severity of pneumonia caused by challenge with a combination of the same serotypes.

EXAMPLE 5

Combined *P. haemolytica* A1, A2 and A6 serotype Vaccine

Organisms of *P. haemolytica* serotypes A1, A2 and A6, strains FA1, FA2 and FA6 respectively, were grown and harvested as described in previous Examples, and incorporated in an AO adjuvant vaccine. Heat killed whole organisms of type A2 were prepared, also as previously described. Capsule extracts of strains FA1 and FA6 were prepared by sodium salicylate extraction. The sodium salicylate extract was centrifuged at 40,000 g for 30 minutes and the supernatant dialysed against 0.02 M phosphate and 0.03 M sodium chloride at pH 7.6 for 48 hours, and was concentrated to 1/10 of its volume by ultra-filtration through XM 100 A Diaflo Amicon membrane (Amicon Limited, High Wycombe, Buckinghamshire, England). The concentrate was tested for in vitro antigenic activity by an IHA test and the dry matter concentration determined after further dialysis against distilled water. The capsule extracts and HKO were incorporated into AO adjuvant as described previously, to give a vaccine containing 0.18 mg/ml of A1 capsule extract, 0.75 mg/ml of A2 HKO and 0.21 mg/ml of A6 capsule extract.

Sixty-four, 2 or 4 weeks old, SPF lambs were randomly allocated into eight groups, four groups to be vaccinated and paired control groups, such that the age lambs were challenged by exposure to an aerosol of *P. haemolytica*. Vaccinated and paired unvaccinated control groups were exposed in randomly allocated groups of four to aerosols of strains FA1, FA2, FA6 and FA9 respectively, the strain FA1 aerosol containing $3.8 \times 10^4$, FA2 $1.2 \times 10^4$, FA6 $1 \times 10^3$ and FA9 $3.1 \times 10^4$ organisms/liter.

Surviving lambs were killed 7 days after challenge. Clinical examinations and post mortem examination of lung lesions were assessed as in previous Examples, and the results obtained, together with the statistical analysis of the results as determined by the Mann-Whitney ranking test, are given below in Table 5.

The results obtained indicate that the combined A1, A2 and A6 serotype vaccine provides good protection against challenge with A1 and A6 serotype and also some measure of protection against challenge with the A2 serotype. It is believed that the level of protection against A2 challenge may be increased by altering the concentration of the A2 HKO antigenic material in the vaccine.

TABLE 5

Clinical, Pneumonic Lesion and Total Scores in lambs inoculated with *P. haemolytica* vaccine and challenged as indicated

| | Challenge | No. of lambs | No. died of killed | Mean clinical score (range) | Mean lesion score (range) | Mean Total score (range) |
|---|---|---|---|---|---|---|
| Vaccinated | | | | 5.5* (0–16) | 6.6 (0–20) | 12.2 (0–36) |
| | A1 | | | | | |
| Control | | 8 | 4 | 12.8 (4–18) | 11.8 (5–20) | 24.7 (14–38) |
| Vaccinated | | 9 | 1 | 4.6 (1–14) | 6.6 (0–10) | 11.3 (0–19) |
| | A2 | | | | | |
| Control | | 8 | 0 | 9.5 (0–10) | 11.2 (5–20) | 20.7 (5–30) |
| Vaccinated | | 8 | 0 | 1.3 (0–6) | 2.5* (0–5) | 3.8* (0–8) |
| | A6 | | | | | |
| Control | | 8 | 1 | 4.2 (0–11) | 9.3 (5–20) | 13.6 (0–31) |
| Vaccinated | | 9 | 2 | 6.3 (3–15) | 10.5 (5–20) | 16.8 (8–35) |
| | A9 | | | | | |
| Control | | 7 | 3 | 9.5 (0–17) | 10 (5–20) | 19.5 (5–35) |

TABLE 5-continued

Clinical, Pneumonic Lesion and Total Scores in lambs inoculated with P. haemolytica vaccine and challenged as indicated

| Challenge | No. of lambs | No. died of killed | Mean clinical score (range) | Mean lesion score (range) | Mean Total score (range) |
| --- | --- | --- | --- | --- | --- |

*Significant difference at 5% level.

The results obtained in the foregoing Examples are summarised in terms of the ratio of the group mean total score of vaccinates to that of controls in Table 6 below, giving an indication of the relative protection afforded by the various vaccines investigated. The result of 0.90 for the A9 serotype in the trivalent vaccine case, i.e. Example 5 above, arises from the fact that A9 represents a heterologous challenge as it was not present in the vaccine.

TABLE 6

PROTECTION EXPRESSED AS: —
$$\frac{\text{GROUP MEAN TOTAL SCORE OF VACCINATES}}{\text{GROUP MEAN TOTAL SCORE OF CONTROLS}}$$

VACCINES

| MONOVALENT | DIVALENT | TRIVALENT |
| --- | --- | --- |
|  | A1 CE, A2 HKO CFA | A1, A6, CE A2 HKO/AO |
| A1 CE/CFA 0.4 | A1 0.45 | A1 0.45 |
| A6 CE/CFA 0.37 |  | A2 0.55 |
| A2 HKO/AO 0.38 |  | A6 0.28 |
| A2 CE/CFA 0.50 |  | A9 0.90 |
| A2 CE/AO 1.0 |  |  |
| A2 HKO |  |  |
| + A2 CE/AO 0.43 |  |  |
| A9 CE/AO 0.19 |  |  |

We claim:

1. A pasteurellosis vaccine comprising antigenic material derived from the A1 and A2 serotypes of *Pasteurella haemolytica*, wherein the A1 serotype antigenic material comprises capsular extract and the A2 serotype antigenic material comprises heat-killed whole organisms.

2. The vaccine according to claim 1, comprising additional antigenic material selected from the group consisting of the A6 serotype of *P. haemolytica*, the A9 serotype of *P. haemolytica*, the A7 serotype of *P. haemolytica* and mixtures thereof.

3. The vaccine according to claim 1 or 2 further comprising *P. haemolytica* T serotype antigenic material.

4. The vaccine according to claim 1 further comprising antigenic material from *P. multocida*.

5. The vaccine according to claim 2 or 4 wherein the additional antigenic material comprises capsular extract.

6. The vaccine according to claim 3 wherein the additional antigenic material comprises capsular extract.

7. The vaccine according to claim 1 wherein the A2 antigenic material comprises A2 capsular extract together with A2 heat-killed whole organism.

8. The vaccine according to claim 1 wherein the capsular extract antigenic material comprises protein and lipopolysaccharide antigenic material in addition to capsule polysaccharide antigenic material.

9. The vaccine according to claim 8 in which capsular extract antigenic material comprises salicylate extract antigenic material.

10. The vaccine according to claim 1 further comprising an aluminum hydroxide gel/oil adjuvant.

11. The vaccine according to claim 1, in dosage form, comprising from about 0.1 up to about 20 mg of antigenic material per dose.

12. The vaccine according to claim 11 comprising from about 0.5 up to about 10 mg of antigenic material per dose of each serotype included within the vaccine.

13. A process for the production of a pasteurellosis vaccine comprising: cultivating organisms of the A1 and A2 serotype of *P. haemolytica*; preparing antigenic material of the A2 serotype by heat-killing whole organisms of the A2 serotype; preparing antigenic material of the A1 serotype by forming a capsular extract from organisms of the A1 serotype; and admixing said antigenic materials of the A1 and A2 serotypes.

14. The process according to claim 13 wherein capsular extract antigenic material of the A2 serotype of *P. haemolytica* is incorporated into the vaccine as well as the A2 heat-killed whole organism antigenic material.

15. The process according to claim 13 or 14 wherein capsular extract antigenic material is prepared by salicylate treatment of organisms comprising: contacting the organisms with a salicylate solution having a concentration in the range from about 0.1 M up to about 10 M, for a period from about 1 up to about 5 hours; separating cell debris from the solution; and then concentrating and purifying the soluble antigenic material.

16. The process according to claim 15 wherein the salicylate solution contacted with the organisms has a concentration of about 1 M and is contacted with the organisms for about 3 hours.

17. The process according to claim 13 wherein the heat-killed whole organisms are prepared by heat treatment of live organisms at a temperature of at least 50° C. for a period of at least 10 minutes.

18. The process according to claim 13 wherein the antigenic material is absorbed on to aluminum hydroxide gel which is then emulsified in oil.

19. A method for use in agricultural animal husbandry for the prevention and control of pasteurellosis in sheep, cattle and other animals comprising vaccinating the animals with a vaccine according to claim 1 or 2 in an amount effective to control pasteurellosis.

20. A method according to claim 19 wherein vaccination is carried out soon after birth to provide the animals with protection against pasteurellosis at an early stage.

21. The method according to claim 20 wherein vaccination is carried out at least four weeks after birth.

22. The method according to claim 19 wherein sheep flocks are vaccinated in late spring with a vaccine comprising said *P. haemolytica* A serotype antigenic material to provide protection against summer outbreaks of pneumonic pasteurellosis.

* * * * *